(12) United States Patent
Zimmer et al.

(10) Patent No.: US 6,323,369 B1
(45) Date of Patent: Nov. 27, 2001

(54) SUBSTITUTED CYCLOHEPTENES, THEIR PREPARATION AND USE

(75) Inventors: Oswald Zimmer; Wolfgang Werner Alfred Strassburger, both of Wuerselen; Werner Guenter Englberger, Stolberg; Babette-Yvonne Koegel, Langerwehe-Hamich, all of (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 09/460,717

(22) Filed: Dec. 14, 1999

(30) Foreign Application Priority Data

Dec. 14, 1998 (DE) .............................. 198 57 475

(51) Int. Cl.⁷ ....................... C07C 211/00; A61K 31/135
(52) U.S. Cl. ........................ 564/337; 564/443; 514/646
(58) Field of Search ..................... 564/443, 337; 514/646

(56) References Cited

U.S. PATENT DOCUMENTS 3,830,934   8/1974  Flick et al. .................... 424/330

FOREIGN PATENT DOCUMENTS 1518663   12/1969  (DE) .
6610022 *  2/1967  (NL) .

* cited by examiner

Primary Examiner—Samuel Barts
(74) Attorney, Agent, or Firm—Crowell & Moring LLP

(57) ABSTRACT

This invention provides substituted cycloheptenes of the general formula I

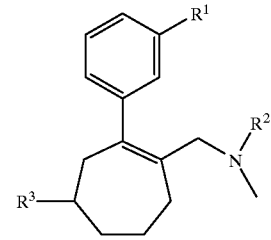

in which $R^1$ represents OH, O-$(C_1-C_6)$-alkyl, O-$(C_3-C_7)$-cycloalkyl, O-aryl, $C_1-C_6$-alkyl-COO-, aryl-COO-, $R^2$ represents $C_1-C_6$-alkyl, $(CH_2)_{(1-2)}$-aryl, $C_2-C_6$-alkenyl-aryl and $R^3$ represents $(CH_2)_{(0-1)}$-$C_5$-$C_7$-cycloalkyl, $(CH_2)_{(0-2)}$-aryl, heterocyclyl, $C_1-C_6$-alkyl-heterocyclyl either as a racemate or in the form of the pure enantiomers, each as a base or as a salt with a pharmaceutically acceptable acid, a process for their preparation and their use as medicaments.

11 Claims, No Drawings

SUBSTITUTED CYCLOHEPTENES, THEIR PREPARATION AND USE

The invention provides substituted cycloheptenes of the general formula I

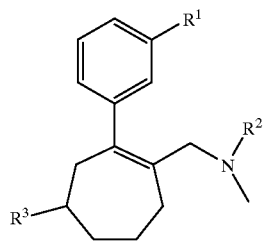

in which
R[1] represents OH, O—(C$_1$–C$_6$) -alkyl, O—(C$_3$–C$_7$) -cycloalkyl, O-aryl, C$_1$–C$_6$alkyl-COO—, aryl-COO—,
R[2] represents C$_1$–C$_6$-alkyl, (CH$_2$)$_{(1-2)}$-aryl, C$_2$–C$_6$-alkenyl-aryl and
R[3] represents (CH$_2$)$_{(0-1)}$—C$_5$–C$_7$-cycloalkyl, (CH$_2$)$_{(0-2)}$-aryl, heterocyclyl, C$_1$–C$_6$-alkyl-heterocyclyl,
either as a racemate or in the form of the pure enantiomers, each as a base or as a salt with a pharmaceutically acceptable acid, a process for their preparation and their use as medicaments.

Classical opioids such as morphine are very effective during the treatment of severe to very severe pain. However, their use is restricted due to the known side-effects, e.g. respiratory depression, vomiting, sedation, obstipation and the development of tolerance. In addition they are less effective in the case of neuropathic or incidental pains such as those suffered in particular by tumour patients.

opioids develop their analgesic effect by bonding to receptors located in the membrane, these belonging to the family of so-called G-protein coupled receptors. The biochemical and pharmacological characterisation of subtypes of these receptors has now led to the hope that subtype-specific opioids may provide a different effect/side-effect profile from e.g. morphine. Whereas morphine bonds selectively to the so-called μ-receptors, endogenous encephalines have been characterised as δ-selective peptides. Further pharmacological tests have now demonstrated the probable existence of more subtypes of these opioid receptors ($μ_1, μ_2, κ_1, κ_2, κ_3, δ_1$ and $δ_2$).

Knowledge relating to the physiological significance of δ-receptor selective substances has been substantially extended by the discovery of the non-peptidic antagonist naltrindol. It has now been demonstrated that δ-agonists have an intrinsic antinociceptive potential. In addition to a number of animal experimental studies, there have also been trials with the peptidic agonists D-alanine[2]-D-leucine[5]-encephalin (DADL) in cancer patients for whom morphine was no longer having an analgesic effect. Following intrathecal administration, DADL exhibited a long-lasting analgesic effect.

Obviously δ-agonists differ from μ-agonists in their interaction with the "endogenous opioid antagonist" cholecystokinin (CCK). In addition to this different mode of action, the actual side-effects profile of δ-agonists and μ-agonists may differ, e.g. by reducing the respiratory depression or obstipation. These compounds have great potential as analgesics and, quite generally, for all pathological conditions which can normally be treated with δ-opiate receptor agonists.

The object on which the invention is based therefore comprises providing analgesically effective substances whose biological effectiveness is partly or largely promoted via δ-opiate receptor agonists.

It has now been found that these requirements are satisfied by the substituted cycloheptene compounds of the general formula I.

The present invention provides new substituted cycloheptenes of the general formula I

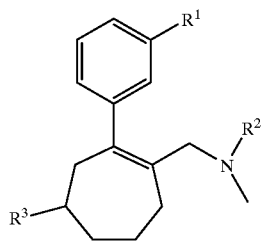

in which
R[1] represents OH, O—(C$_1$–C$_6$)-alkyl, O—(C$_3$–C$_7$)-cycloalkyl, O-aryl, C$_1$–C$_6$-alkyl-COO—, aryl-COO—,
R[2] represents C$_1$–C$_6$-alkyl, (CH$_2$)$_{(1-2)}$-aryl, C$_2$–C$_6$-Alkenyl-aryl and
R[3] represents (CH$_2$)$_{(0-1)}$—C$_5$–C$_7$-cycloalkyl, (CH$_2$)$_{(0-2)}$-aryl, heterocyclyl, C$_1$–C$_6$-alkyl-heterocyclyl
which are present in the form of their enantiomers, diastereomers, racemates or bases or as salts of physiologically acceptable acids.

Compounds of the general formula I in which R[1] represents OH, O—(C$_1$–C$_6$)-alkyl, O—(C$_3$–C$_7$)-cycloalkyl, O-aryl, C$_1$–C$_6$-alkyl-COO—, or aryl-COO— and R[2] and R[3] are defined in accordance with the definition for general formula I, or R[1] represents OH, O—(C$_1$–C$_6$)-alkyl or O—(C$_3$–C$_7$)-cycloalkyl, R[2] represents C$_1$–C$_6$-alkyl or (CH$_2$)$_{(1-2)}$-aryl and R[3] is defined in accordance with the definition for general formula I, or R[1] represents OH, R[2] represents C$_1$–C$_6$-alkyl or (CH$_2$)$_{(1-2)}$-aryl and R[3] is defined in accordance with the definition for general formula I, or R[1] represents OH, R[2] represents C$_1$–C$_6$-alkyl and R[3] is defined in accordance with the definition for general formula I are preferred.

Particularly preferred compounds include the following:
3-[6-(4-chlorophenyl)-2-dimethylaminomethyl-cyclohept-1-enyl]-phenol hydrochloride
3-(2-dimethylaminomethyl-6-phenyl-cyclohept-1-enyl)-phenol hydrochloride
3-(2-dimethylaminomethyl-6-naphth-1-yl-cyclohept-1-enyl)-phenol hydrochloride
3-(2-dimethylaminomethyl-6-naphth-2-yl-cyclohept-1-enyl]-phenol hydrochloride
3-[2-dimethylaminomethyl-6-(4-hydroxyphenyl)-cyclohept-1-enyl]-phenol hydrochloride
3-(2-dimethylaminomethyl-6-m-toluyl-cyclohept-1-enyl]-phenol hydrochloride
3-[6-(3-tert-butyl-phenyl)-2-dimethylaminomethyl-cyclohept-1-enyl]-phenol hydrochloride
6-[4-dimethylaminomethyl]-3-(3-hydroxyphenyl)-cyclohept-3-enyl]-naphth-2-ol hydrochloride
3-[2-dimethylaminomethyl-6-(3-fluoro-4-hydroxyphenyl)-cyclohept-1-enyl]-phenol hydrochloride 3-[2-dimethylaminomethyl-6-(2-hydroxyphenyl)-cyclohept-1-enyl]-phenol hydrochloride 3-(6-cyclohexyl-2-dimethylaminomethyl-cyclohept-1-enyl)-phenol hydrochloride 3-(6-cyclohexylmethyl-2-dimethylaminomethyl-cyclohept-1-enyl)-phenol hydrochloride 3-(6-benzyl-2-dimethylaminomethyl-cyclohept-1-enyl)-phenol hydrochloride 3-[2-dimethylaminomethyl)-6-(3-hydroxybenzyl)-cyclohept-1-enyl]-phenol hydrochloride 3-(2-dimethylaminomethyl)-6-phenethyl-cyclohept-1-enyl)-phenol hydrochloride 3-[2-dimethylaminomethyl)-6-(3,5-dimethyl-4-hydroxyphenyl)-cyclohept-1-enyl]-phenol hydrochloride 3-[2-dimethylaminomethyl-6-(3-hydroxyphenyl)-cyclohept-1-enyl]-phenol hydrochloride 3-[2-(methylphenethylaminomethyl)-6-phenyl-cyclohept-1-enyl]-phenol hydrochloride and

[2-(3-methoxyphenyl)-4-naphth-1-yl-cyclohept-1-enyl-methyl]-dimethylamine hydrochloride.

The expression "$C_1$–$C_6$-alkyl" in the present invention means straight chain or branched hydrocarbons with 1 to 6 carbon atoms. The following may be mentioned by way of example:

methyl, ethyl, propyl, isopropyl, n-butyl, sec-butyl, tert-butyl, n-pentyl, neopentyl and n-hexyl.

In the context of the present invention the expression "$C_2$–$C_6$-alkenylene" means straight chain or branched hydrocarbons with 2 to 6 carbon atoms which contain one or more double bonds. Examples are 2-propenyl, 2-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 2-hexenyl, 3-hexenyl, 4-hexenyl, 5-hexenyl, 1-methyl-2-pentenyl or 1,3-dimethyl-3-butenyl.

The expression "aryl" in the context of the present invention means unsubstituted phenyls or phenyls which are substituted once or several times by OH, F, Cl, $CF_3$, $C_1$–$C_6$-alkyl, $C_1$–$C_6$-alkoxy, $C_1$–$C_7$-cycloalkoxy, $C_3$–$C_7$-cycloalkyl, $C_2$–$C_6$-alkenylene or heterocyclyl units. The heterocyclyl or phenyl groups may optionally be fused. The expression may optionally also mean naphthyl.

The expression "heterocyclyl" in the context of the present invention is understood to mean 5- or 6-membered saturated or unsaturated, optionally provided with a fused aryl system, heterocyclic compounds which contain one or two hetero atoms from the group nitrogen, oxygen and/or sulfur.

Examples of saturated heterocyclyl compounds are 1,4-dioxan, tetrahydrofuran and 1,4-thioxan.

The following may be mentioned by way of example from the group of unsaturated heterocyclyl compounds; furan, thiophene, pyridine, pyrimidine, thiazole, oxazole, isoxazole, pyridazine, pyrazine, quinoline, isoquinoline, phthalazine and quinazoline.

The expression "$C_1$–$C_6$-alkylheterocyclyl" in the context of the present invention means that the "heterocyclyl" groups as defined above are bonded via a $C_1$–$C_6$ alkyl group.

The expression "$C_2$–$C_6$-alkenylenaryl" in the context of the present invention means that the aryl groups as defined above are bonded via a $C_2$–$C_6$-alkenylene group.

The expression "silanyl compound" in the context of the present invention is understood to mean trialkylsilyl or triarylsilyl, dialkylarylsilyl or diarylalkylsilyl group which are used as protective groups for the hydroxyl function. Examples which may be mentioned are triethylsilyl, tripropylsilyl, dimethylphenylsilyl, ditert-butylphenylsilyl, triisopropylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl or propyldiphenylsilyl.

The invention also provides a process for preparing compounds of the general formula I which is characterised by reacting a tertiary alcohol of the general formula II,

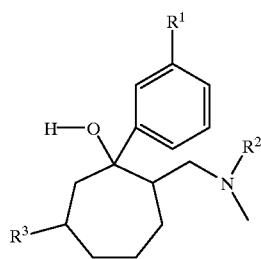

II in which $R^1$ to $R^3$ are defined in the same way as for formula I, with semi-concentrated or concentrated organic or inorganic acids such as e.g. hydrochloric acid, hydrobromic acid, formic acid, or solutions of hydrogen bromide in acetic acid at temperatures of 20° C. to 110° C., wherein the tertiary alcohols of the formula II are obtained by reacting aminoketones of the general formula III

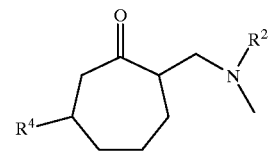

III wherein $R^2$ is defined in the same way as given above and $R^4$ is defined in the same way as for $R^3$ with the exception that an optionally present hydroxyl function is present in a protected form such as e.g. as a benzyloxy- or silanyloxy-group, with an organometallic compound of the formula IV

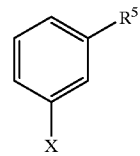

IV in which X represents MgCl, MgBr, MgI or Li and $R^5$ is defined in the same way as for $R^1$ with the exception that like $R^4$ an optionally present hydroxyl function is present in the protected form such as e.g. as a benzyloxy- or silanyloxy-group, to produce a compound of the general formula IIa

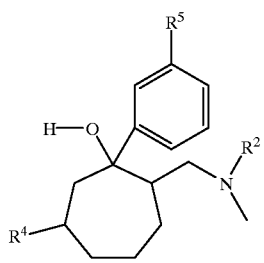

which is then converted into a compound of the general formula II.

Compounds of the general formula III are obtained from cycloheptanones of the general formula (V)

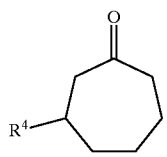

in which $R^4$ is defined in the same way as above, by reaction with amines of the general formula $HN(CH_3)R^2$ (optionally in the form of their salts) and paraformaldehyde or an aqueous formaldehyde solution in solvents such as water, alcohols or acetic acid at temperatures between 20° C. and the boiling point of the solvent. Preparation of the compounds of the general formula III however preferably takes place by reacting V with methylenimmonium halides of the general formula $H_2C=N(CH_3)R^2X$, wherein $R^2$ is defined in the same way as above and X represents a chlorine or iodine atom, in solvents such as acetonitrile or tetrahydrofuran at temperatures of 20° C. to 50° C.

Reaction of compounds III and IV is performed in an aliphatic ether, for example diethylether and/or tetrahydrofuran, at temperatures from –70° C. to +60° C. Compounds of the formula IV in which X represents a lithium atom are obtained from compounds of the formula IV in which X represents Br or I by halogen-lithium exchange using e.g. an n-butyllithium/n-hexane solution.

Several methods are available for converting a compound of the formula IIa into one of the formula II, depending on the identity of $R^5$ or of the protective group in $R^4$.

If $R^5$ represents a benzyloxy group and/or a benzyloxy group is present in $R^4$, then this expediently takes place by reductive debenzylation with catalytically activated hydrogen, wherein platinum or palladium absorbed on a support material such as active carbon, are used as catalyst. The reaction is performed in a solvent such as acetic acid or a $C_1$–$C_4$-alkylalcohol at pressures of 1 to 100 bar and temperatures of +20° C. to +100° C., wherein the compound IIa is preferably present in the form of one of its salts.

If $R^5$ is a silanyloxy group and/or a silanyloxy group is present in $R^4$, elimination of the protective group is achieved by reacting the corresponding compound of the formula IIa with tetra-n-butylammonium fluoride at +20° C. in an inert solvent such as tetrahydrofuran, dioxan or diethylether or by treatment with a methanolic solution of hydrogen chloride.

If $R^5$ is a methoxy group or $R^4$ in a compound of the formula IIa contains a methoxy group, the compounds of the formula II in which $R^1$ represents a hydroxyl group and/or $R^3$ contains a hydroxyl group can be prepared by reacting with diisobutylaluminium hydride in an aromatic hydrocarbon such as toluene at a temperature between 60° C. and 130° C. In this case the analogous compound of the formula I can also be obtained directly by heating IIa either with a solution of hydrogen bromide in glacial acetic acid or concentrated hydrobromic acid. This is also possible by reacting IIa with methansulfonic acid/methionine at temperatures between 20° C. and 50° C.

In compounds of the formula I in which $R^1$ represents a methoxy group and/or a methoxy group is contained in $R^3$, these can also be converted into the hydroxyl function by reaction with diisobutylaluminium hydride in the same way as described above.

Compounds of the general formula I in $R^1$ represents a hydroxyl function can be converted into an ester function in ways known per se.

Compounds of the formula I can be converted into their salts using physiologically acceptable acids such as hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid in a manner known per se. Salt production is preferably performed in a solvent such as diethylether, diisopropylether, an alkyl acetate, acetone and/or 2-butanone. Trimethylchlorosilane in an aqueous solution is particularly suitable for preparing hydrochlorides.

δ-Opiate receptor bonding tests

Tests on determining the affinity of compounds of the formula I according to the invention for the δ-opiate receptor were performed in brain membrane homogenates (homogenate from rat brain without the cerebellum, pons and medulla oblongata from male Wistar rats). In this case, freshly prepared rat brain was homogenised each time, cooled by ice, in 50 mmol/l of tris-HCl (tris-(hydroxymethyl)-aminomethane hydrochloride) (pH 7.4) and centrifuged for 10 min at 5,000 g and 4° C. After decanting and discarding the supernatant liquid, the membrane sediment was again taken up in 50 mmol/l of tris-HCl (pH 7.4) and homogenised and the homogenate was then centrifuged for 20 min at 20,000 g and 4° C. This wash stage was repeated once more. Then the supernatant liquid was decanted and the membrane sediment was homogenised in cold 50 mmol/l tris-HCl, 20% glycerol (w:v), 0.01% bacitracin (w/v) (pH 7.4) and frozen in portions until tested. For the receptor bonding tests, the portions were thawed out and diluted 1:10 with the bonding test buffer. A 50 mmol/l tris-HCl, 5 mmol/l $MgCl_2$ (pH 7.4) supplemented with 0.1% (w:v) of bovine serum albumin was used as buffer, and 1 nmol/l of ($^3$H)-2-D-ala-deltorphin II was used as a radioactive ligand in the bonding test. The proportion of non-specific bonding was determined in the presence of 10 mmol/l of naloxon. In further batches, the compounds according to the invention were added in a number of concentrations and the displacement of the radioactive ligand from its specific bond was determined. Three identical batches were incubated for 90 min at 37° C. and then harvested in order to determine the radioactive ligand bonded to the membrane homogenate by means of filtration through a glass fibre filter (GF/B). The radioactivity of the glass fibre filter discs was measured in a beta-counter by adding a scintillator. The affinity of compounds according to the invention for the δ-opiate receptor was calculated as $IC_{50}$ in accordance with the law of mass action using non-linear regression. The K values in table 1 are given as the average value plus or minus the standard deviation of 3 quite independent trials.

TABLE 1

| Example Number | δ-opiate receptor bonding $K_i$ [nmol/l] |
|---|---|
| 1 | 1.4 ± 0.8 |
| 2a | 30.3 ± 4.7 |
| 2b | 3.8 ± 0.2 |
| 2c | 24.7 ± 2.4 |
| 2d | 31.5 ± 5.9 |
| 2e | 15.2 ± 4.3 |
| 2f | 3.2 ± 0.8 |
| 2g | 17.5 ± 5.2 |
| 2h | 19.4 ± 4.7 |
| 2i | 14.6 ± 2.2 |
| 2j | 24.7 ± 3.1 |
| 2k | 10.3 ± 2.2 |
| 2l | 28.6 ± 5.8 |
| 2m | 10.2 ± 1.0 |
| 2n | 7.4 ± 2.2 |
| 2o | 30.6 ± 10.5 |
| 2p | 2.5 □ 0.7 |
| 3 | 8.3 ± 3.3 |

Testing the anti-nociceptive activity in a writhing test in mice

The anti-nociceptive effectiveness was tested in phenylquinone-induced writhing in mice, modified by I. C.Hendershot, J. Forsaith, J. Pharmacol. Exp. Ther. 125, 237–240 (1959). Here, male NMRI mice with a weight of 25–30 g were used. 10 min after intravenous administration of a compound according to the invention, 0.3 ml/mouse of a 0.02% strength aqueous solution of phenylquinone was administered intraperitoneally to groups of 10 animals per substance dose (phenylbenzoquinone, Sigma, Deisenhofen; solution prepared by adding 5% ethanol and storing in a water bath at 45° C.). The animals were placed individually in observation cages. Using a push button counter,the number of pain-induced stretching movements (so-called writhing reactions=straightening the body while stretching out the back extremities) was counted 5–20 min after administration of the phenylquinone. From the dose-dependent decrease in writhing reactions as compared with groups of animals tested in parallel to which no compounds according to the invention had been administered, the $ED_{50}$ values for the writhing reaction were calculated using regression analysis (evaluation programme Martens EDV service, Eckental).

TABLE 2

| Example Number | Writhing test, mice $ED_{50}$ i.v. [mg/kg] (95% confidence range) |
|---|---|
| 1 | 3.31 (2.70–3.88) |
| 2a | 7.40 (5.53–9.21) |
| 2b | 4.48 (3.36–6.27) |
| 2c | 5.29 (4.11–7.17) |
| 2d | 7.56 (5.49–10.70) |
| 2e | 2.25 (1.56–3.00) |
| 2h | 6.22 (4.68–8.28) |
| 2i | 0.89 (0.62–1.29) |
| 3 | 3.40 (2.40–4.92) |

EXAMPLES

The examples below are given to explain the present invention in more detail without however restricting it.

The stationary phase used for column chromatography was silica gel 60 (0.040–0.063 mm) from the company E. Merck, Darmstadt.

The thin layer chromatography tests were performed using HPTLC ready-made plates, silica gel 60 F 254 from E. Merck, Darmstadt.

The mixing ratios in the mobile solvent for all chromatographic tests are always given as vol/vol.

The expression tris-HCl means tris-(hydroxymethyl)-aminomethane hydrochloride.

(w/v) weight/volume

Example 1

3-[2-(dimethylaminomethyl-6-(3-hydroxyphenyl)-cyclohept-1-enyl]-phenol hydrochloride 1st stage (3-methoxy-phenyl)-cycloheptanone To a freshly prepared Grignard solution of 5.83 g of magnesium shavings and 28.7 ml of 1-bromo-3-methoxybenzene in 675 ml of anhydrous diethylether at 20° C., with stirring, were added first 20.95 g of copper(I) iodide, then dropwise a solution of 15.2 g of cyclohept-2-enone (80%) in 175 ml of anhydrous diethylether. After complete addition, the mixture was heated for 45 min under reflux. Then the product was decomposed by the dropwise addition of 85 ml of a saturated ammonium chloride solution. After diluting with 200 ml of water, the organic phase was separated and the aqueous phase was extracted twice using 100 ml of diethylether each time. The combined organic phases were washed once each with saturated solutions of sodium hydrogen carbonate and sodium chloride, dried over sodium sulfate and evaporated under vacuum. The residue was purified on a chromatography column using diethylether/n-hexane=1/4, finally 1/1, as eluant and 16.5 g (68.6% of theory) of the title compound was thus obtained as a pale yellow oil.

2nd stage 2-dimethylaminomethyl-6-(3-methoxyphenyl)-cycloheptanone hydrochloride 7.2 g of N,N-dimethylmethylenimmonium chloride and 3 drops of acetyl chloride were added to a solution of 16.4 g of the product from stage 1 in 150 ml of acetonitrile and the mixture was stirred for 48 hours at 20° C. The mixture was then diluted with 100 ml of diethylether, the crystalline product was isolated, washed with diethylether and dried under vacuum at 40° C. 21.9 g (93.6% of theory) of the title compound were obtained in the form of white crystals.

melting point: 130–134.5° C.

3rd stage 2-dimethylaminomethyl-1,6-bis-(3-methoxyphenyl)-cycloheptanol

To a freshly prepared Grignard solution consisting of 4.42 ml of 1-bromo-3-methoxybenzene and 0.90 g of magnesium shavings in 35 ml of anhydrous tetrahydrofuran, was added dropwise at 20° C., with stirring, a solution of 9.1 g of the free base of the product from stage 2 in 52 ml of anhydrous tetrahydrofuran. The mixture was then heated under reflux. After reaction had terminated the mixture was worked up in the same way as described in stage 1. After purification on a chromatography column using ethyl acetete/methanol=5/1 as eluant, 10.44 g (82,4% of theory) of the title compound were obtained as an almost colourless oil.

4th stage

3-[2-(dimethylaminomethyl-6-(3-hydroxyphenyl)-cyclohept-enyl]-phenol hydrochloride 10.35 g of the product from stage 3 were heated under stirring with 120 ml of a solution of hydrogen bromide in glacial acetic acid (33% HBr) for 5 hours at 100–110° C. The mixture was then evaporated under vacuum, the residue was taken up in 150 ml of water and made alkaline (pH 9–10) with dilute caustic soda solution (about 5%). This was extracted 3 times using 100 ml of ethyl acetate each time, the combined extracts were washed once with saturated sodium chloride solution, dried over sodium sulfate and evaporated under vacuum. The residue was purified on a chromatography column using ethyl acetate as eluant.

3.71 g (40.7% of theory) of the free base of the title compound were obtained and this was converted into the hydrochloride using trimethylchlorosilane/water in 2-butanone.

Melting point: from 110° C. with decomposition

Example 2

The following compounds were obtained using corresponding starting compounds and the procedure described in example 1, stages 1–4, optionally by varying the reaction conditions (solvent, temperature):

2a: 3-[6-(4-chlorophenyl)-2-dimethylaminomethyl-cyclohept-1-enyl]-phenol hydrochloride
Melting point: from 134° C. with decomposition 2b: 3-(2-dimethylaminomethyl-6-phenyl-cyclohept-1-enyl)-phenol hydrochloride
Melting point: 162–166° C.

2c: 3-(2-dimethylaminomethyl-6-naphth-1-yl-cyclohept-1-enyl)-phenol hydrochloride 2d: 3-(2-dimethylaminomethyl-6-naphth-2-yl-cyclohept-1-enyl]-phenol hydrochloride
Melting point: 183° C.

2e: 3- [2-dimethylaminomethyl-6-(4-hydroxyphenyl)-cyclohept-1-enyl]-phenol hydrochloride
Melting point: 240–242° C.

2f 3-(2-dimethylaminomethyl-6-m-toluyl-cyclohept-1-enyl]-phenol hydrochloride
Melting point: 231–233° C.

2g: 3- [6-(3-tert-butyl-phenyl)-2-dimethylaminomethyl-cyclohept-1-enyl]-phenol hydrochloride
Melting point: 215–218° C.

2h: 6- [4-dimethylaminomethyl)-3-(3-hydroxyphenyl)-cyclohept-1-enyl]-naphth-2-ol hydrochloride
Melting point: from 190° C. with decomposition 2i: 3-[2-dimethylaminomethyl-6-(3-fluoro-4-hydroxyphenyl)-cyclohept-1-enyl]-phenol hydrochloride
Melting point: 227–230° C.

2j: 3-[2-dimethylaminomethyl-6-(2-hydroxyphenyl)-cyclohept-1-enyl]-phenol hydrochloride
Melting point: from 125° C. with decomposition 2k: 3-(6-cyclohexyl-2-dimethylaminomethyl-cyclohept-1-enyl)-phenol hydrochloride
Melting point: 224–225.5° C.

2l: 3-(6-cyclohexylmethyl-2-dimethylaminomethyl-cyclohept-1-enyl)-phenol hydrochloride
Melting point: 203–206° C.

2m: 3-(6-benzyl-2-dimethylaminomethyl-cyclohept-1-enyl)-phenol hydrochloride
Melting point: 208–212° C.

2n: 3-[2-dimethylaminomethyl)-6-(3-hydroxybenzyl)-cyclohept-1-enyl]-phenol hydrochloride
Melting point: 88° C.

2o: 3-(2-dimethylaminomethyl-6-phenethyl-cyclohept-1-enyl)-phenol hydrochloride
Melting point: 188–190° C.

2p: 3-[2-dimethylaminomethyl)-6-(3,5-dimethyl-4-hydroxyphenyl)-cyclohept-1-enyl]-phenol hydrochloride
Melting point: from 156° C. with decomposition Example 3

3-{2-[(methylphenethylamino)-methyl]-6-phenyl-cyclohept-1-enyl}-phenol hydrochloride 1st stage 2-[(methylphenethylamino)-methyl]-6-phenyl-cycloheptanone hydrochloride A mixture of 2.77g of 3-phenylcycloheptanone, 2.52 g of methylphenethylamine hydrochloride and 1.23 ml of an aqueous formaldehyde solution (36%) were heated on a water bath for 2 hours under vigorous stirring and with the introduction of nitrogen. The mixture was then evaporated under vacuum, the residue was extracted 3 times with diethylether/n-hexane=1/1 and dried under vacuum. 5.4 g of the crude title compound were then obtained.

2nd stage 1-(3-methoxyphenyl)-2-[(methylphenethylamino)-methyl]-6-phenyl-cyclohentanol 4.7 g of the free base of the product from stage 1, 2.76 g of 1-bromo-3-methoxybenzene and 0.4 g of magnesium shavings were reacted as described in example 1, stage 3. After a similar working up process and purification on a chromatography column using ethyl acetate/n-hexane=1/1 as eluant, 3.1 g (49.9% of theory) of the title compound were obtained as a yellow oil.

3rd stage

3-{2-[(methylphenethylamino)-methyl]-6-phenyl-cyclohept-1-enyl}-phenol hydrochloride 2.67 g of the products from stage 2 were reacted with a solution of hydrogen bromide in glacial acetic acid (33% HBr) in the same way as described in example 1, stage 4. Following a similar working up process, 1.24 g (50.2% of theory) of the free base of the title compound were obtained and this was converted into the hydrochloride using trimethylchlorosilane in 2-butanone.

Melting point: from 105° C. with decomposition

Example 4

[2-(3-methoxyphenyl-4-naphth-1-yl-cyclohept-1-enyl-methyl]-dimethylamine hydrochloride 4.04 g of 2-dimethylaminomethyl-1-(3-methoxyphenyl)-6-naphth-1-yl-cycloheptanol (product from example 2c, stage 3) were stirred with 50 ml of 6N hydrochloric acid for 24 hours at 50° C. The mixture was made alkaline with caustic soda solution and extracted 3 times using 50 ml of ethyl acetate each time. The extracts were washed with saturated sodium chloride solution, dried over sodium sulfate and evaporated under vacuum. The residue was purified on a chromatography column using ethyl acetate/methanol= 4/1 as eluant, wherein 2.94 g (76.3% of theory) of the free base of the title compound were obtained and this was converted into the hydrochloride using trimethylchlorosilane/water in 2-butanone.

What is claimed is:

1. A substituted cycloheptene compound corresponding to the formula I:

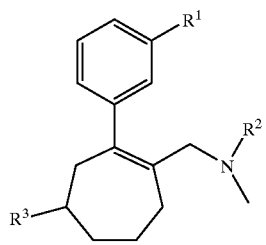

wherein $R^1$ represents OH, O—($C_1$–$C_6$)-alkyl, O—($C_3$–$C_7$)-cycloalkyl, O-aryl, $C_1$–$C_6$-alkyl-COO— or aryl-COO—;

$R^2$ represents $C_1$–$C_6$-alkyl, $(CH_2)_{(1-2)}$-aryl, or $C_2$–$C_6$-alkenyl-aryl; and $R^3$ represents $(CH_2)_{(0-1)}$—$C_3$–$C_7$-cycloalkyl, $(CH_2)_{(0-2)}$-aryl, heterocyclyl, $C_1$–$C_6$-alkyl-heterocyclyl, or a salt thereof with a physiologically acceptable acid.

2. A compound according to claim 1, wherein said compound is in the form of an isolated enantiomer.

3. A compound according to claim 1, wherein said compound is in the form of an isolated diastereomer.

4. A compound according to claim 1, wherein said compound is in the form of a racemic mixture.

5. A compound according to claim 1, wherein:

$R^1$ represents OH, O—($C_1$–$C_6$)-alkyl, or O—($C_3$–$C_7$)-cycloalkyl, and $R^2$ represents $C_1$–$C_6$-alkyl, or $(CH_2)_{(1-2)}$-aryl.

6. A compound according to claim 5, wherein $R^1$ represents OH.

7. A compound according to claim 6, wherein $R^2$ represents $C_1$–$C_6$-alkyl.

8. A compound according to claim 1, wherein said compound is selected from the group consisting of:

3-[6-(4-chlorophenyl)-2-dimethylaminomethyl-cyclohept-1-enyl]-phenol hydrochloride, 3-(2-dimethylaminomethyl-6-phenyl-cyclohept-1-enyl)-phenol hydrochloride, 3-(2-dimethylaminomethyl-6-naphth-1-yl-cyclohept-1-enyl)-phenol hydrochloride, 3-(2-dimethylaminomethyl-6-naphth-2-yl-cyclohept-1-enyl)-phenol hydrochloride, 3-(2-dimethylaminomethyl-6-(4-hydroxyphenyl)-cyclohept-1-enyl)-phenol hydrochloride, 3-(2-dimethylaminomethyl-6-m-toluyl-cyclohept-1-enyl)-phenol hydrochloride, 3-[6-(3-tert-butylphenyl)-2-dimethylaminomethyl-cyclohept-1-enyl]-phenol hydrochloride, 6-[4-dimethylaminomethyl-3-(3-hydroxyphenyl)-cyclohept-1-enyl]-naphth-2-ol hydrochloride, 3-[2-dimethylaminomethyl-6-(3-fluoro-4-hydroxyphenyl)-cyclohept-1-enyl]-phenol hydrochloride, 3-[2-dimethylaminomethyl-6-(2-hydroxyphenyl)-cyclohept-1-enyl]-phenol hydrochloride, 3-(6-cyclohexyl-2-dimethylaminomethyl-cyclohept-1-enyl)-phenol hydrochloride, 3-(6-cyclohexylmethyl-2-dimethylaminomethyl-cyclohept-1-enyl)-phenol hydrochloride, 3-(6-benzyl-2-dimethylaminomethyl-cyclohept-1-enyl)-phenol hydrochloride, 3-[2-dimethylaminomethyl-6-(3-hydroxybenzyl)-cyclohept-1-enyl]-phenol hydrochloride, 3-(2-dimethylaminomethyl)-6-phenethyl-cyclohept-1-enyl)-phenol hydrochloride, 3-(2-dimethylaminomethyl)-6-(3,5-dimethyl-4-hydroxyphenyl)-cyclohept-1-enyl]-phenol hydrochloride, 3-[2-dimethylaminomethyl-6-(3-hydroxyphenyl)-cyclohept-1-enyl]-phenol hydrochloride, 3-{2-[(methylphen-ethylamino)methyl]-6-phenyl-cyclohept-1-enyl]-phenol hydrochloride, and

[2-(3-methoxyphenyl)-4-naphth-1-yl-cyclohept-1-enyl-methyl]-dimethylamine hydrochloride.

9. A process for preparing a compound corresponding to the formula I:

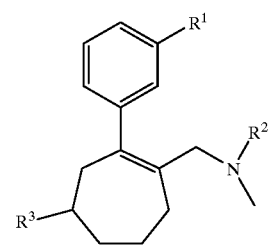

wherein $R^1$ represents OH, O—($C_1$–$C_6$)-alkyl, O—($C_3$–$C_7$)-cycloalkyl, O-aryl, $C_1$–$C_6$-alkyl-COO— or aryl-COO—;

$R^2$ represents $C_1$–$C_6$-alkyl, $(CH_2)_{(1-2)}$-aryl, or $C_2$–$C_6$-alkenylaryl; and $R^3$ represents $(CH_2)_{(0-1)}$—$C_3$–$C_7$-cycloalkyl, $(CH_2)_{(0-2)}$-aryl, heterocyclyl, or $C_1$–$C_6$-alkyl-heterocyclyl, said process comprising the steps of:

reacting an amino ketone corresponding to the formula III:

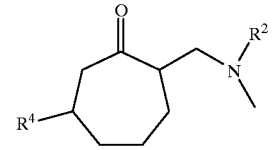

wherein $R^2$ has the meaning given above, and $R^4$ has the same meaning as $R^3$ with the exception that if a hydroxy group is present it is protected by a benzyloxy- or silanyloxy-group, with an organometallic compound corresponding to the formula IV:

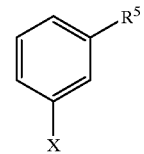

wherein x represents MgCl, MgBr, MgI or Li, and $R^5$ has the same meaning as $R^1$ with the exception that if a hydroxy group is present it is protected by a benzyloxy- or silanyloxy-group, to obtain a compound corresponding to

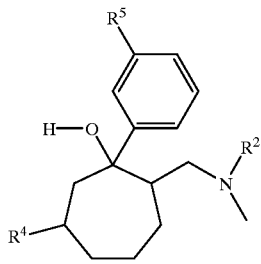

the formula IIa:

wherein $R^2$, $R^4$ and $R^5$ have the meanings given above;

converting the compound of Formula IIa to a tertiary alcohol corresponding to the Formula II:

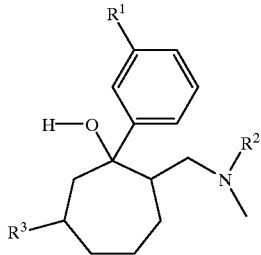

wherein $R^1$, $R^2$ and $R^3$ have the meanings given above; and reacting the tertiary alcohol of Formula II with an acid at a temperature in the range from 20° C. to 110° C. to obtain the compound of formula I.

10. A pharmaceutical composition comprising a pharmaceutically effective amount of a compound corresponding to the formula I:

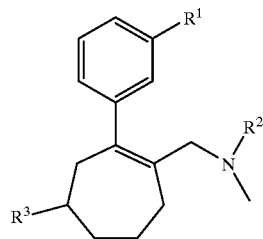

wherein
$R^1$ represents OH, O—($C_1$–$C_6$)-alkyl, O—($C_3$–$C_7$)-cycloalkyl, O-aryl, $C_1$–$C_6$-alkyl-COO— or aryl-COO—;
$R^2$ represents $C_1$–$C_6$-alkyl, $(CH_2)_{(1-2)}$-aryl, or $C_2$–$C_6$-alkenyl-aryl; and
$R^3$ represents $(CH_2)_{(0-1)}$—$C_3$–$C_7$-cycloalkyl, $(CH_2)_{(0-2)}$-aryl, heterocyclyl, $C_1$–$C_6$-alkyl-heterocyclyl, or a physiologically acceptable acid addition salt
thereof, and at least one pharmaceutical carrier or adjuvant.

11. A method of treating a mammal in need of analgesic treatment, said method comprising administering to said mammal an analgesically effective amount of a compound corresponding to the formula I:

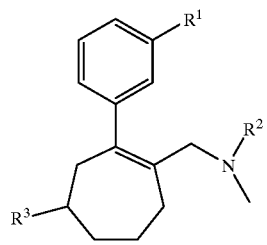

wherein
$R^1$ represents OH, O—($C_1$–$C_6$)-alkyl, O—($C_3$–$C_7$)-cycloalkyl, O-aryl, $C_1$–$C_6$-alkyl-COO— or aryl-COO—;
$R^2$ represents $C_1$–$C_6$-alkyl, $(CH_2)_{(1-2)}$-aryl, or $C_2$–$C_6$-alkenyl-aryl; and
$R^3$ represents $(CH_2)_{(0-1)}$—$C_3$–$C_7$-cycloalkyl, $(CH_2)_{(0-2)}$-aryl, heterocyclyl, $C_1$–$C_6$-alkyl-heterocyclyl,
or a physiologically acceptable acid addition salt thereof.

* * * * *